(12) United States Patent
Suh et al.

(10) Patent No.: US 11,872,546 B2
(45) Date of Patent: Jan. 16, 2024

(54) CATALYST FOR HYDROGENATION REACTION AND METHOD FOR PRODUCING SAME

(71) Applicants: LG CHEM, LTD., Seoul (KR); KOREA ADVANCED INSTITUTE OF SCIENCE AND TECHNOLOGY, Daejeon (KR)

(72) Inventors: Myungji Suh, Daejeon (KR); Dong Hyun Ko, Daejeon (KR); Minkee Choi, Daejeon (KR); Kyunglim Hyun, Jeju-do (KR)

(73) Assignee: LG Chem, Ltd., Seoul (KR)

( * ) Notice: Subject to any disclaimer, the term of this patent is extended or adjusted under 35 U.S.C. 154(b) by 41 days.

(21) Appl. No.: 17/432,455

(22) PCT Filed: Jul. 13, 2020

(86) PCT No.: PCT/KR2020/009187
§ 371 (c)(1),
(2) Date: Aug. 19, 2021

(87) PCT Pub. No.: WO2021/066300
PCT Pub. Date: Apr. 8, 2021

(65) Prior Publication Data
US 2022/0118432 A1   Apr. 21, 2022

(30) Foreign Application Priority Data
Sep. 30, 2019   (KR) .................. 10-2019-0120801

(51) Int. Cl.
*B01J 31/06* (2006.01)
*B01J 23/44* (2006.01)
(Continued)

(52) U.S. Cl.
CPC ............... *B01J 31/06* (2013.01); *B01J 23/44* (2013.01); *C07C 5/09* (2013.01); *C08F 26/06* (2013.01);
(Continued)

(58) Field of Classification Search
None
See application file for complete search history.

(56) References Cited

U.S. PATENT DOCUMENTS

| 2008/0300436 A1 | 12/2008 | Cheung et al. |
| 2012/0004467 A1 | 1/2012 | Kramer et al. |

(Continued)

FOREIGN PATENT DOCUMENTS

| CN | 102463117 A | 5/2012 |
| CN | 104415715 A | 3/2015 |

(Continued)

OTHER PUBLICATIONS

International Search Report from PCT/KR2020/009187, dated Oct. 22, 2020.
(Continued)

*Primary Examiner* — Yun Qian
(74) *Attorney, Agent, or Firm* — Bryan Cave Leighton Paisner LLP

(57) ABSTRACT

A catalyst for a hydrogenation reaction including: a polymer support; and a catalytic component supported on the polymer support. The polymer support includes a repeating unit represented by Formula 1 or 2.

7 Claims, 10 Drawing Sheets

(51) Int. Cl.
*C07C 5/09* (2006.01)
*C08F 26/06* (2006.01)

(52) U.S. Cl.
CPC ...... *C07C 2523/44* (2013.01); *C07C 2531/06* (2013.01)

(56) References Cited

U.S. PATENT DOCUMENTS

| | | |
|---|---|---|
| 2013/0331524 A1 | 12/2013 | Soddemann et al. |
| 2015/0231612 A1 | 8/2015 | Dai et al. |
| 2015/0266015 A1 | 9/2015 | Choi et al. |

FOREIGN PATENT DOCUMENTS

| | | |
|---|---|---|
| CN | 104689830 A | 6/2015 |
| CN | 107715914 A | 2/2018 |
| CN | 108097329 A | 6/2018 |
| GB | 802100 A | 10/1958 |
| JP | 2006-231318 A | 9/2006 |
| JP | 2014-030821 A | 2/2014 |
| KR | 10-2008-0035616 A | 4/2008 |
| KR | 10-2012-0002464 A | 1/2012 |
| KR | 10-2012-0117252 A | 10/2012 |
| KR | 10-2013-0043213 A | 4/2013 |
| KR | 2013-0044036 A | 5/2013 |
| KR | 10-2015-0041033 A | 4/2015 |
| KR | 10-2015-0109744 A | 10/2015 |
| KR | 10-1684766 B1 | 12/2016 |
| WO | 2016/038454 A1 | 3/2016 |

OTHER PUBLICATIONS

Written Opinion of the ISA from PCT/KR2020/009187, dated Oct. 22, 2020.

Yun et al., "Cross-Linked "Poisonous" Polymer: Thermochemically Stable Catalyst Support for Tuning Chemoselectivity", ACS Catalysis, vol. 6 (2016) pp. 2435-2442.

Patel et al., "Highly Stable Nanoporous Sulfur-Bridged Covalent Organic Polymers for Carbon Dioxide Removal", Advanced Functional Materials, vol. 23 (2013) pp. 2270-2276.

Fan et al. "Palladium Clusters Confined in Triazinyl-Functionalized COFs With Enhanced Catalytic Activity", Applied Catalysis B: Environmental, vol. 257, article No. 117942 (2019) pp. 1-9.

Siebels et al. "Rhodium Nanoparticles Supported on Covalent Triazine-Based Frameworks as Re-Usable Catalyst for Benzene Hydrogenation and Hydrogen Evolution Reaction", Journal of Materials Chemistry A, vol. 7 (2019) pp. 11934-11943.

[Figure 1]
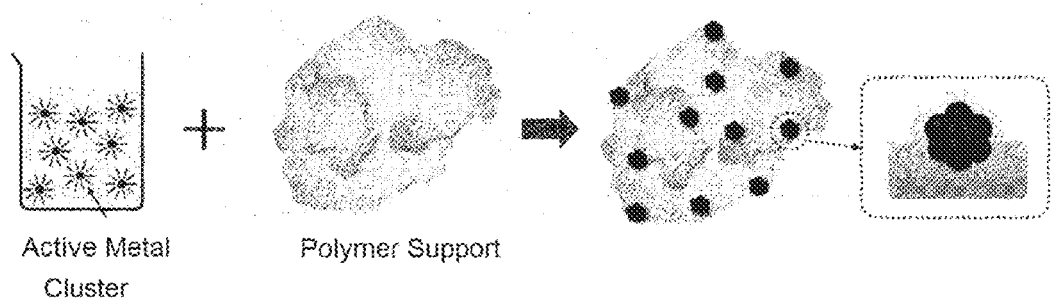

[Figure 2A]
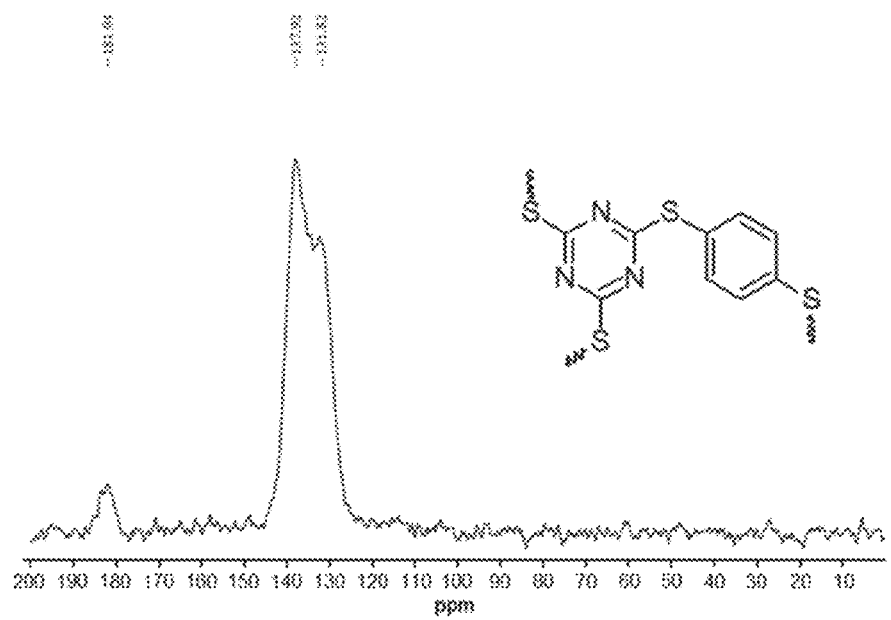
[Figure 2B]
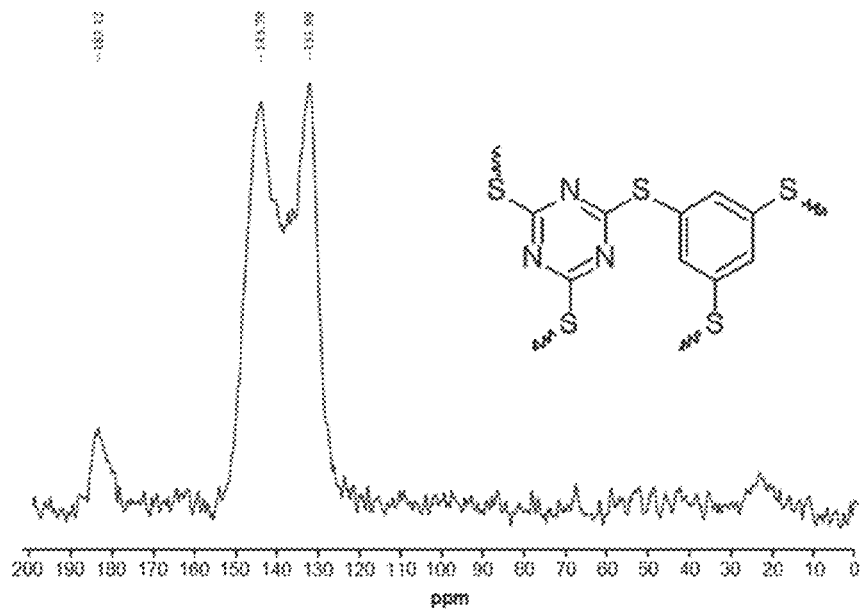

[Figure 3A]
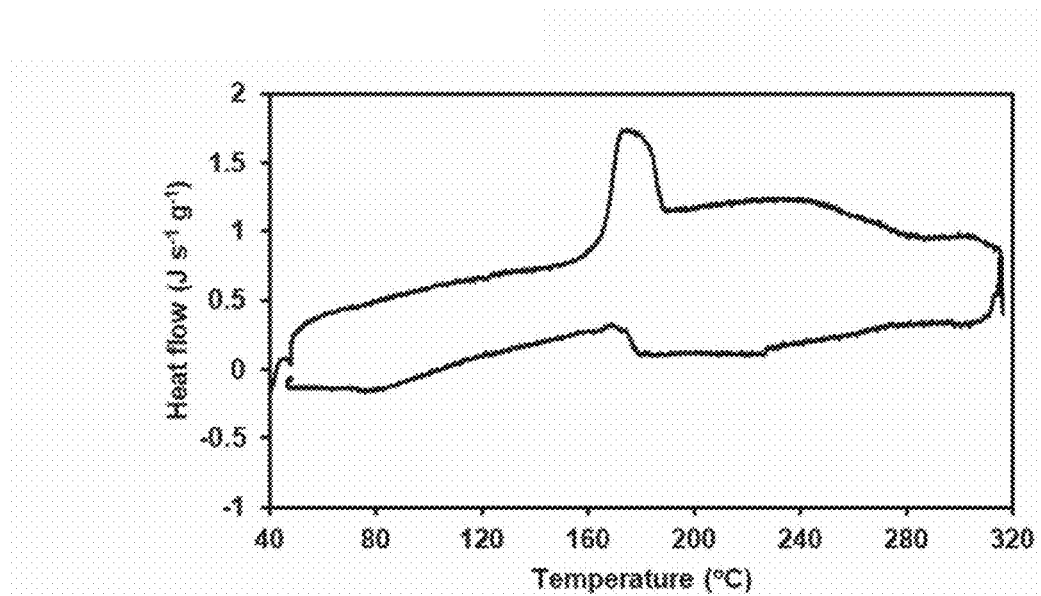
[Figure 3B]
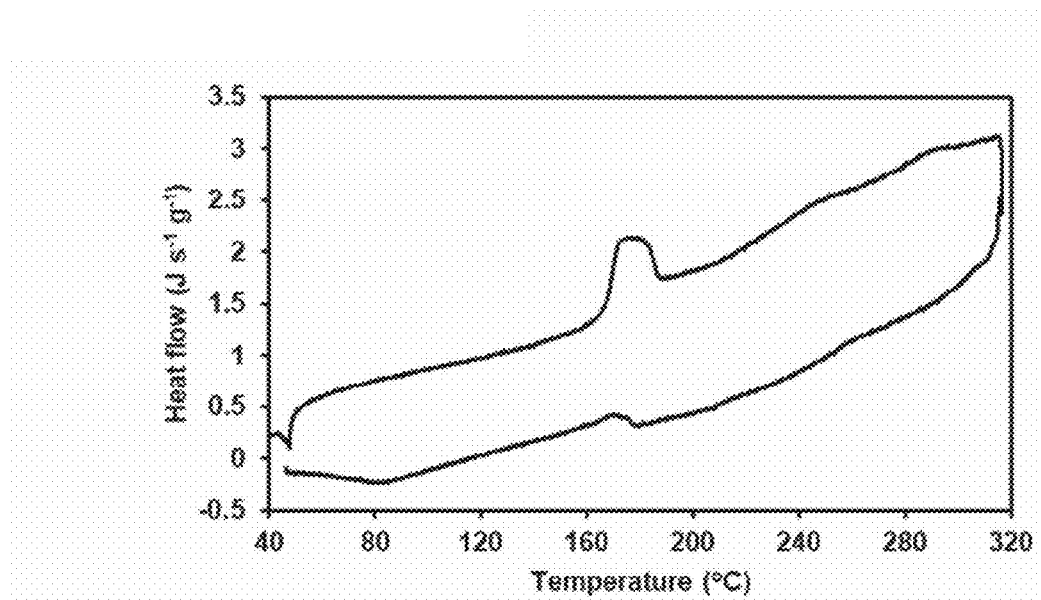

[Figure 4A]
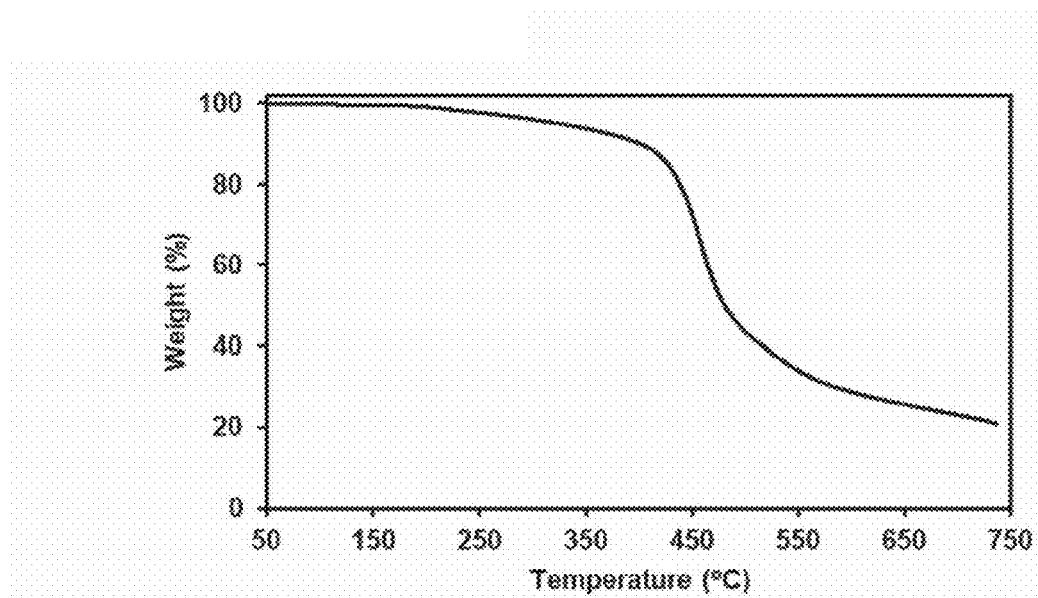
[Figure 4B]
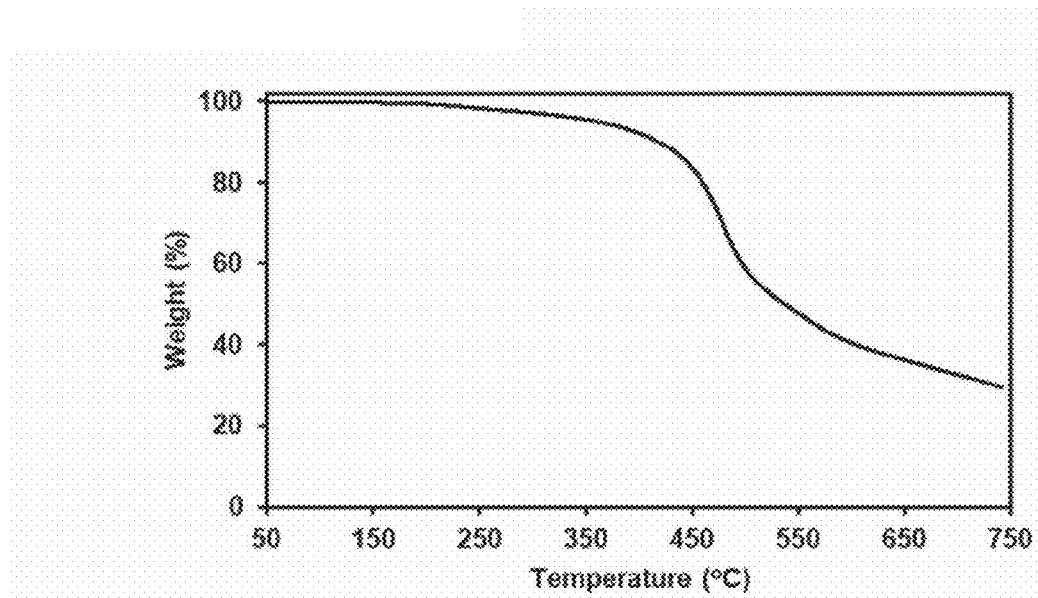

[Figure 5A]
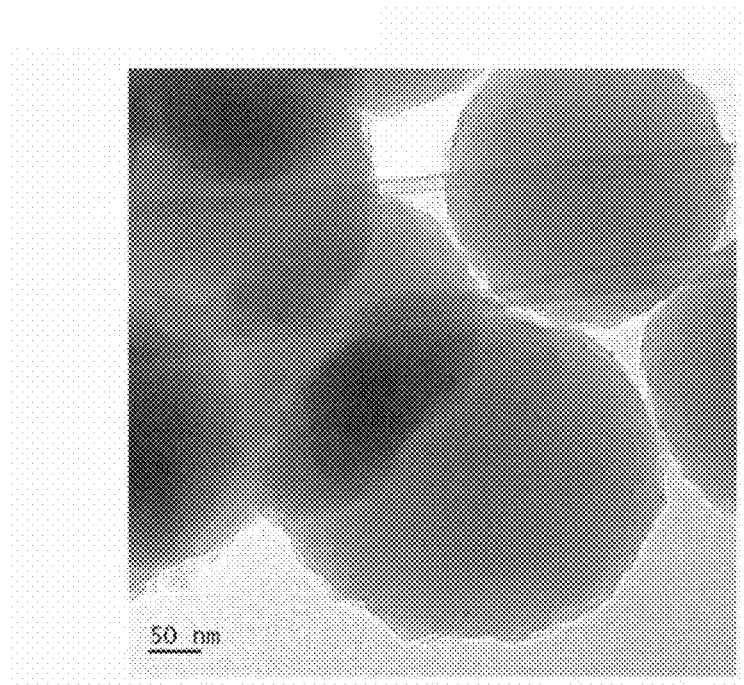
[Figure 5B]
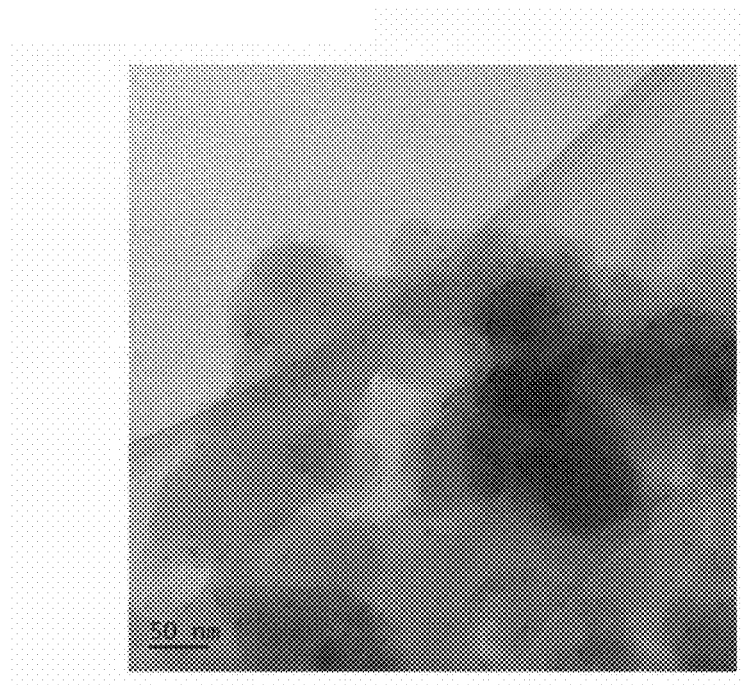

[Figure 6A]
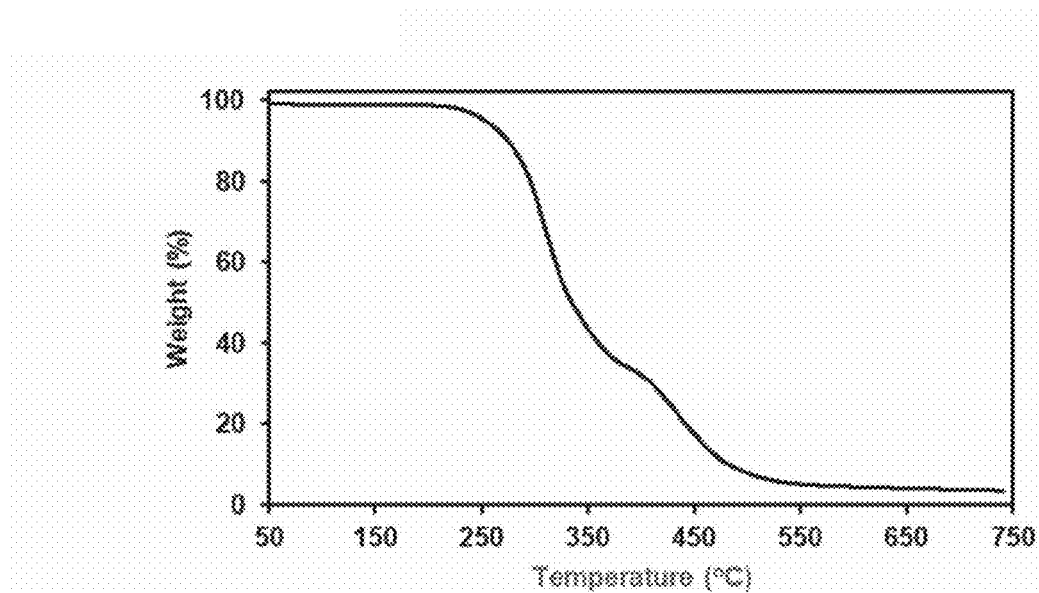
[Figure 6B]
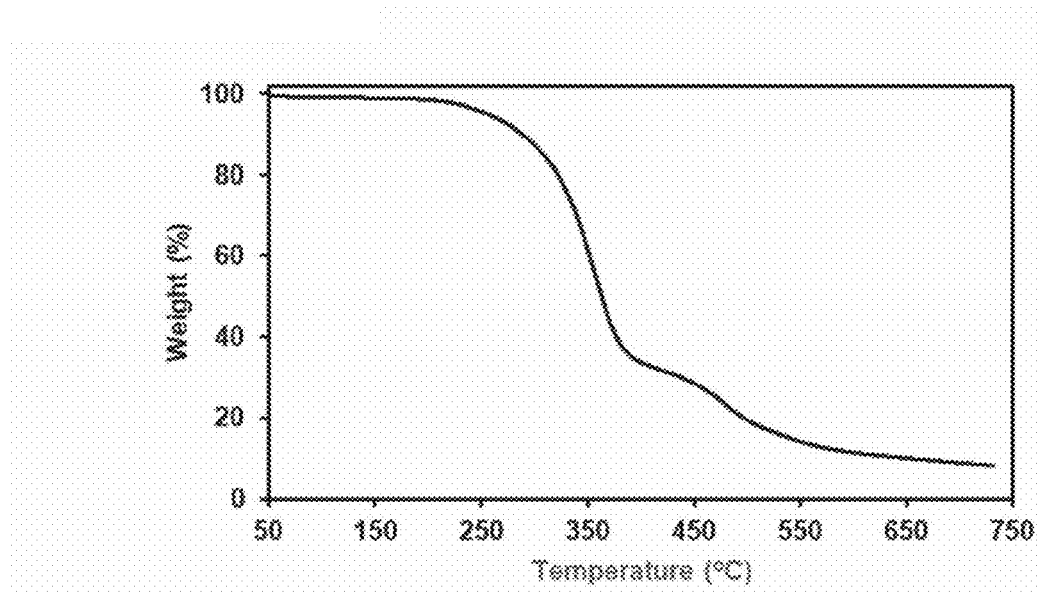

[Figure 7]
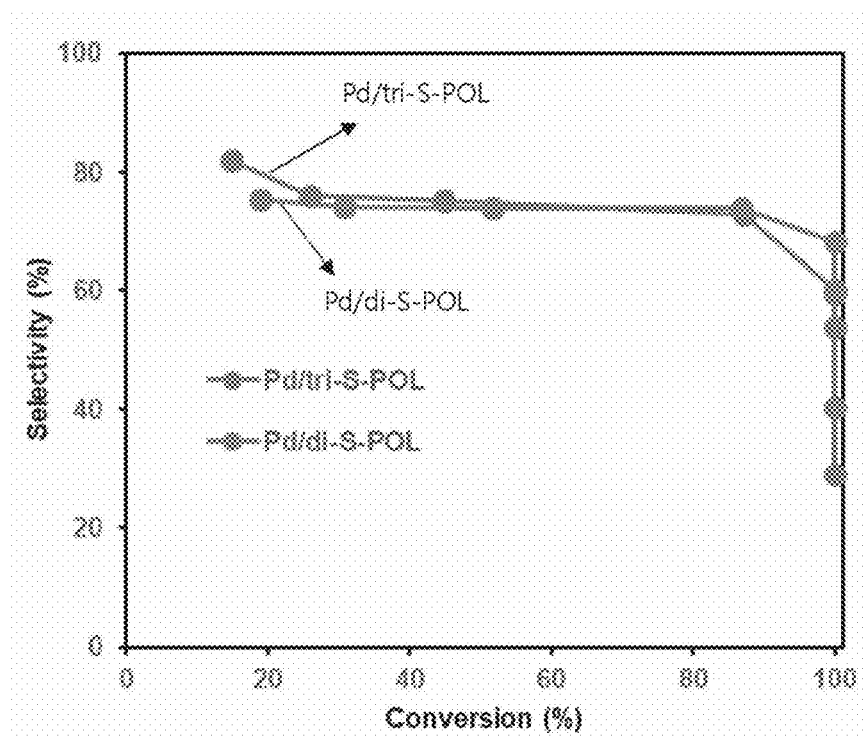

[Figure 8]
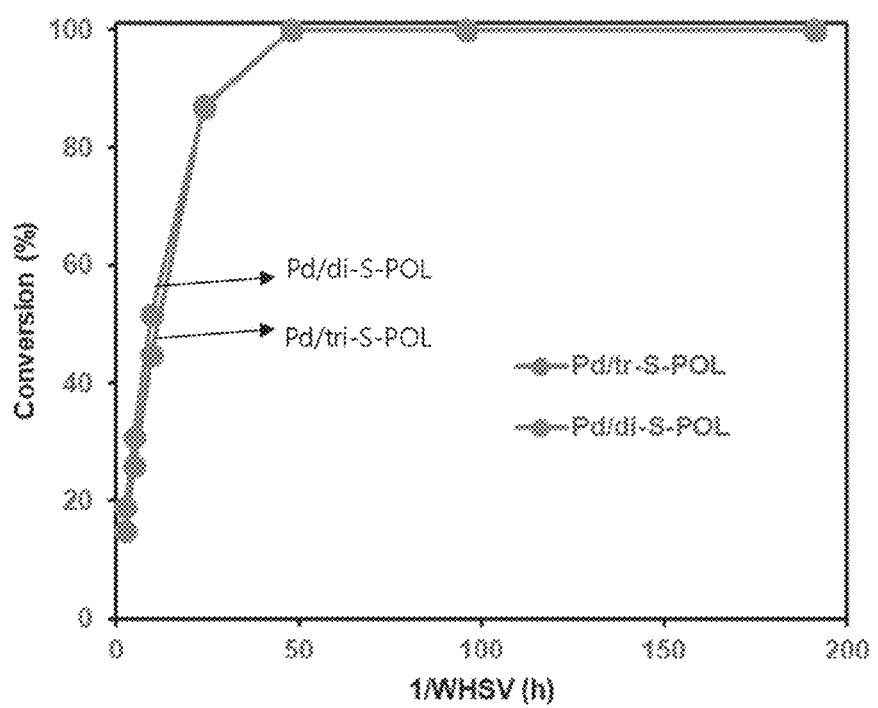

[Figure 9A]
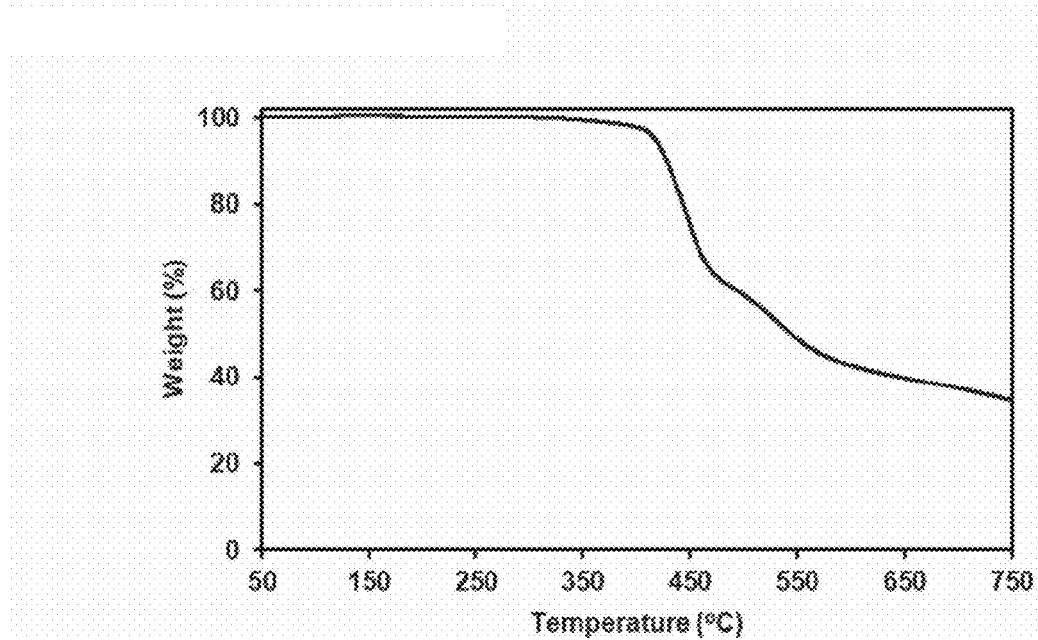
[Figure 9B]
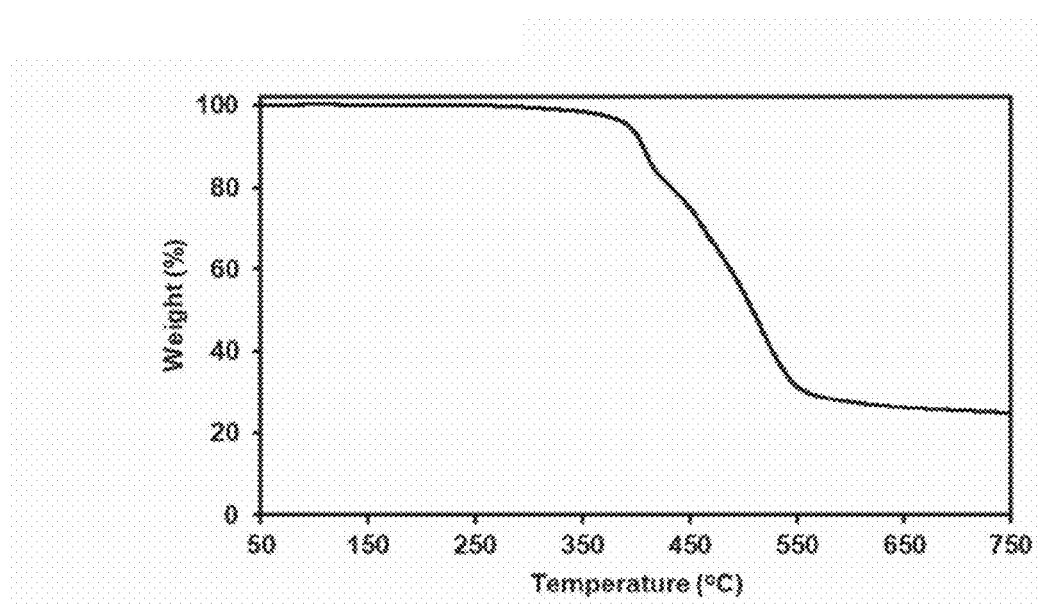

[Figure 10A]
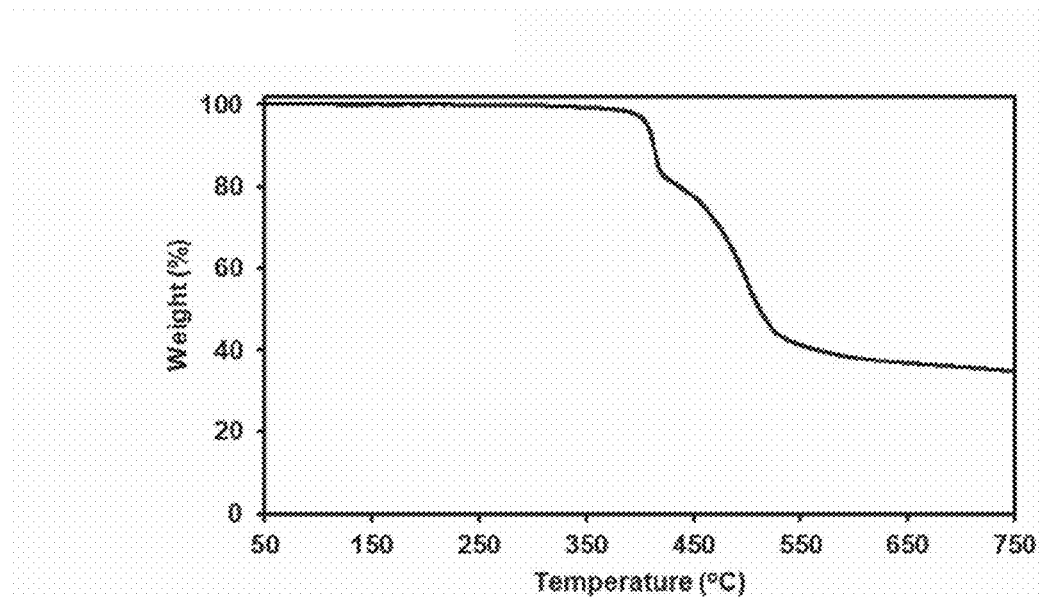
[Figure 10B]
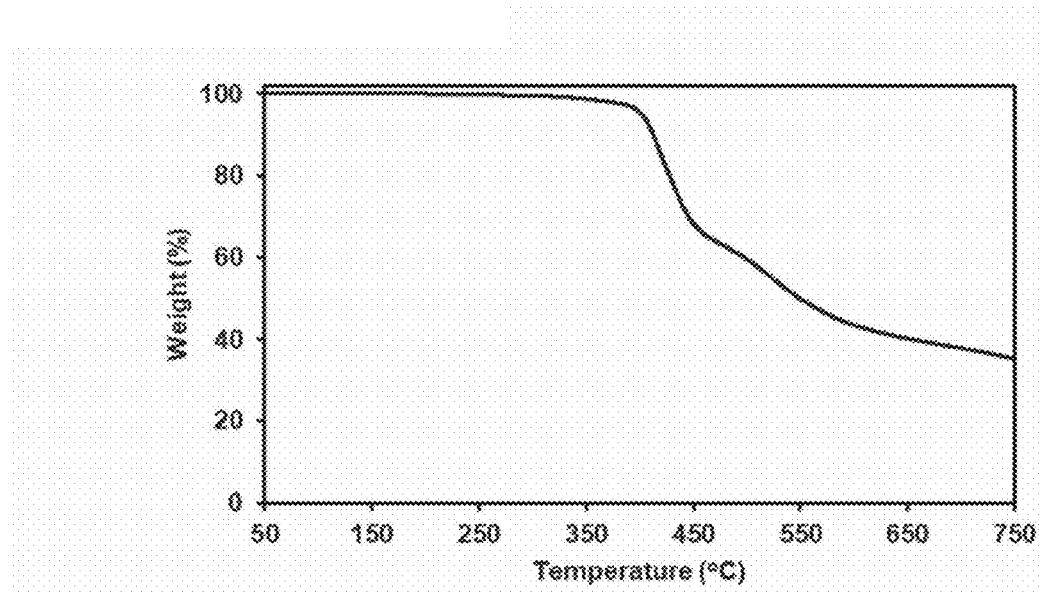

CATALYST FOR HYDROGENATION REACTION AND METHOD FOR PRODUCING SAME

CROSS-REFERENCE TO RELATED APPLICATIONS

This application is a U.S. national stage of international application No. PCT/KR2020/009187, filed on Jul. 13, 2020, and claims priority to and the benefit of Korean Patent Application No. 10-2019-0120801 filed in the Korean Intellectual Property Office on Sep. 30, 2019, the entire contents of which are incorporated herein by reference.

TECHNICAL FIELD

The present invention relates to a catalyst for a hydrogenation reaction and a method for manufacturing the same.

BACKGROUND

Oil refinery and petrochemical plants produce large amounts of hydrocarbons, which contain large amounts of unsaturated hydrocarbons which cause problems during subsequent process steps or storage periods. Examples of these unsaturated hydrocarbons include acetylene, propyne, propadiene, butadiene, vinylacetylene, butyne, phenylacetylene, styrene and the like.

As an example, acetylene is known to reduce the activity of a catalyst in an ethylene polymerization process and cause deterioration in the quality of a polymer. Therefore, in a process of synthesizing polyethylene from ethylene, the concentration of acetylene contained in ethylene raw materials needs to be reduced to a minimal level.

These undesirable unsaturated compounds are usually removed to several PPM or less by a selective hydrogenation reaction. It is very important to enhance the selectivity of a desired compound from a reaction of selectively hydrogenating unsaturated compounds to avoid coke formation, which reduces the reaction activity.

In related art, nickel sulfate, tungsten/nickel sulfate or copper containing catalysts have been used for selective hydrogenation reactions. However, these catalysts have low catalytic activity even at high temperatures, and thus reduce polymer formation. Further, supported palladium (Pd) or Pd and silver (Ag) containing catalysts based on alumina or silica are also used in selective hydrogenation processes, but the selectivity is unsatisfactory or the activity is low.

Therefore, there is a need in the art for developing a catalyst for a hydrogenation reaction, which has excellent selectivity for a product of hydrogenation reaction and excellent catalytic activity.

SUMMARY

The present application provides a catalyst for a hydrogenation reaction and a method for manufacturing the same.

An exemplary embodiment of the present application provides a catalyst for a hydrogenation reaction, the catalyst comprising:
  a polymer support; and
  a catalytic component supported on the polymer support,
  wherein the polymer support comprises a repeating unit represented by the following Formula 1 or 2:

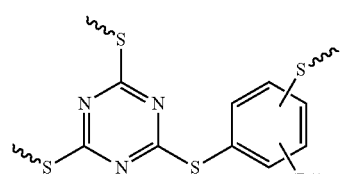

[Formula 1]

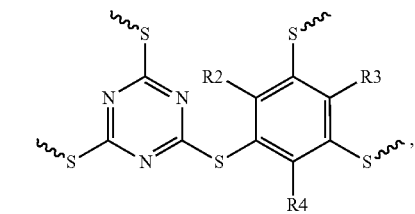

[Formula 2]

In Formulae 1 and 2:
R1 to R4 are the same as or different from each other, and are each independently hydrogen, an alkyl group having 1 to 10 carbon atoms, or an aryl group having 6 to 20 carbon atoms, and
m is an integer from 0 to 4.

Further, another exemplary embodiment of the present application provides a method for manufacturing a catalyst for a hydrogenation reaction, the method comprising:
  preparing a polymer support comprising the repeating unit represented by Formula 1 or 2; and
  supporting a catalytic component on the polymer support.

According to an exemplary embodiment of the present application, a polymer support comprising the repeating unit represented by Formula 1 or 2 can be applied as a support for a catalyst for a hydrogenation reaction.

Further, according to an exemplary embodiment of the present application, the catalyst comprising the polymer support is characterized by having excellent stability in the reaction temperature range of the hydrogenation reaction and being able to improve the selectivity for the product of the hydrogenation reaction.

BRIEF DESCRIPTION OF DRAWINGS

FIG. 1 is a schematic illustration of a method for supporting a catalytic component on a polymer support according to an exemplary embodiment.

FIGS. 2A and 2B are cross polarization magic-angle spinning $^{13}$C nuclear magnetic resonance (CP/MAS $^{13}$C NMR) analysis spectra of the polymers according to Synthesis Examples 1 and 2, respectively.

FIGS. 3A and 3B are differential scanning calorimetry (DSC) analysis spectra of the polymers according to Synthesis Examples 1 and 2, respectively.

FIGS. 4A and 4B are thermal gravimetric analysis (TGA) results of the polymers according to Synthesis Examples 1 and 2, respectively.

FIGS. 5A and 5B are transmission electron microscope (TEM) images of the catalysts according to Examples 1 and 2, respectively.

FIGS. 6A and 6B are thermal gravimetric analysis (TGA) results of the catalysts according to Examples 1 and 2, respectively.

FIG. 7 is a graphical representation of the selectivity of ethylene as relates to the conversion of the acetylenes of Examples 1 and 2.

FIG. 8 is graphical representation of the conversion of the acetylenes of Examples 1 and 2 as relates to the value of 1/WHSV.

FIGS. 9A and 9B are thermal gravimetric analysis (TGA) results of the polymers according to Synthesis Examples 3 and 4, respectively.

FIGS. 10A and 10B are thermal gravimetric analysis (TGA) results of the polymers according to Synthesis Examples 5 and 6, respectively.

DETAILED DESCRIPTION

Hereinafter, the present specification will be described in more detail.

When one member is disposed "on" another member in the present specification, this includes not only a case where the one member is brought into contact with another member, but also a case where still another member is present between the two members.

When one part "comprises" one constituent element in the present specification, unless otherwise specifically described, this does not mean that another constituent element is excluded, but means that another constituent element can be further included.

As described above, it is common to use a catalyst in which Pd is supported on an alumina support as a catalyst for a hydrogenation reaction, as described in related art. However, such related art catalysts have a problem in that the catalyst replacement cycle is short due to the rapid deactivation of the catalyst, and thus process costs are increased. Further, to improve the selectivity of the product of hydrogenation reaction in the related art, a modifier was introduced, but the introduction of the modifier has a problem in that the process cost increases and an additional separation process is required.

Thus, the present application was intended to develop a catalyst for a hydrogenation reaction, which has excellent selectivity for the product of a hydrogenation reaction and excellent catalytic activity. In particular, the present inventors have developed a catalyst comprising a polymer support applied to a catalyst for a hydrogenation reaction.

The catalyst for a hydrogenation reaction according to an exemplary embodiment of the present application comprises: a polymer support; and a catalytic component supported on the polymer support, in which the polymer support comprises a repeating unit represented by the following Formula 1 or 2:

[Formula 1]
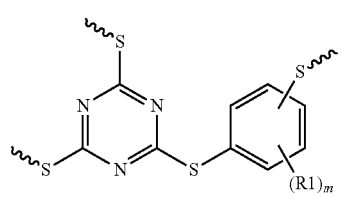

[Formula 2]
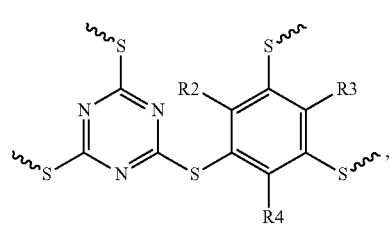

In Formulae 1 and 2:

R1 to R4 are the same as or different from each other, and are each independently hydrogen, an alkyl group having 1 to 10 carbon atoms, or an aryl group having 6 to 20 carbon atoms, and m is an integer from 0 to 4.

In an exemplary embodiment of the present application, "∿∿" in the formulae means a point where the repeating units are linked.

In an exemplary embodiment of the present application, Formula 1 can be represented by any one of the following Formulae 3 to 5 and 7 to 10:

[Formula 3]
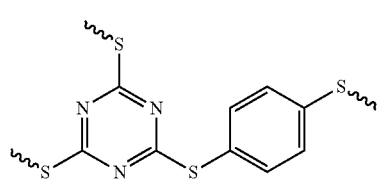

[Formula 4]
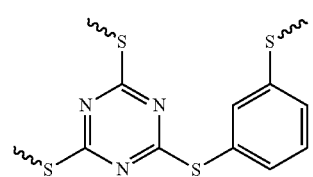

[Formula 5]
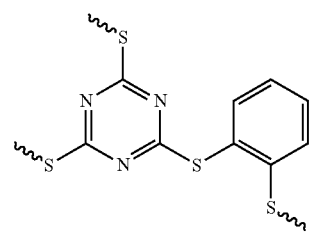

[Formula 7]
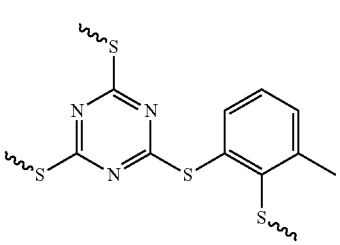

[Formula 8]
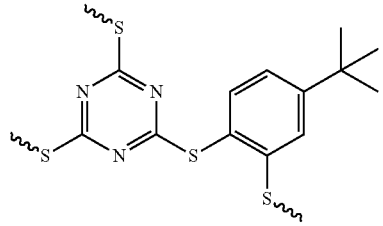

[Formula 9]
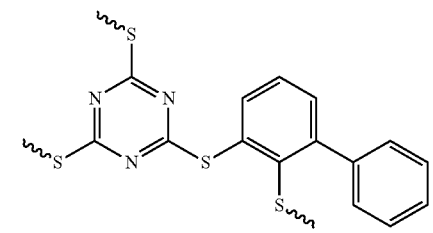

-continued

[Formula 10]
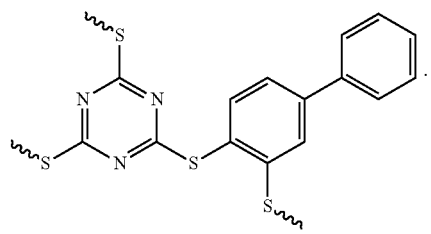

In an exemplary embodiment of the present application, Formula 2 can be represented by any one of the following Formulae 6 and 11 to 13:

[Formula 6]
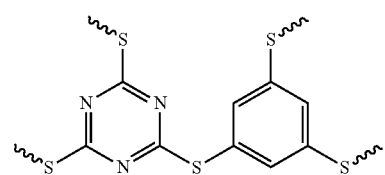

[Formula 11]
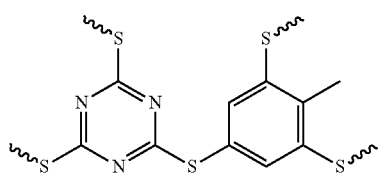

[Formula 12]
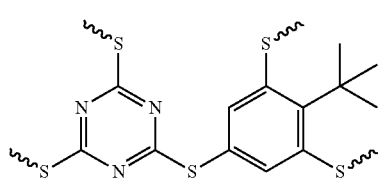

[Formula 13]
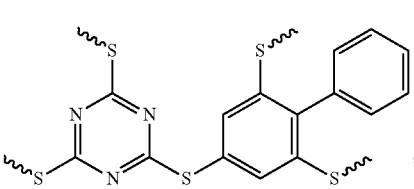

In an exemplary embodiment of the present application, the alkyl groups of Formulae 1 and 2 can be straight-chained or branched, and the number of carbon atoms thereof is not particularly limited, but is preferably 1 to 10. Specific examples of the alkyl group include a methyl group, an ethyl group, a propyl group, an isopropyl group, a butyl group, an n-butyl group, an isobutyl group, a tert-butyl group, a sec-butyl group, a 1-methylbutyl group, a 1-ethylbutyl group, and the like, but are not limited thereto.

In an exemplary embodiment of the present application, specific examples of the aryl groups of Formulae 1 and 2 include a phenyl group, a biphenyl group, a terphenyl group, a quaterphenyl group, a naphthyl group, an anthracenyl group, a phenanthrenyl group, a pyrenyl group, and the like, but are not limited thereto.

In an exemplary embodiment of the present application, all of R1 to R4 of Formulae 1 and 2 can be hydrogen.

In an exemplary embodiment of the present application, the polymer support has a structure in which a triazine ring and a benzene ring are linked to each other by an intermediate linking group (—S—). That is, three —S functional groups bonded to the triazine rings of Formulae 1 and 2 are each bonded to a benzene ring, and one or two —S functional group(s) bonded to the benzene ring has or have a structure in which the —S functional group is bonded to the triazine ring.

In an exemplary embodiment of the present application, the polymer support is composed of a cross-linked polymer, so that the molecular weight of the cross-linked polymer is not specified.

According to an exemplary embodiment of the present application, it is possible to exhibit high selectivity compared to a hydrogenation catalyst using a related art alumina or silica support in a selective hydrogenation reaction such as hydrogenation of alkyne to alkene by supporting a hydrogen active metal (a metal capable of forming hydrogen activated by contact with hydrogen molecules) in the polymer support. As an example, in the hydrogenation reaction of alkyne to alkene, in the case of a related art alumina- or silica-based metal supported catalyst, both alkyne and alkene are easily adsorbed on the surface of the metal, so that hydrogenation of alkyne to alkene and hydrogenation of alkene to alkane are non-selectively accomplished. However, as in an exemplary embodiment of the present application, when the polymer support is used, the surface of an active metal is surrounded by the polymer due to the strong binding power between the polymer support and the active metal. Therefore, based on the active metal, a reactant exhibiting a relatively stronger binding power than the binding power between the active metal and the polymer support, such as an alkyne, is adsorbed on the active metal, but reactants exhibiting a relatively weaker binding power, such as alkene, cannot be adsorbed on the active metal. Due to these characteristics, a catalyst having an active metal supported on a polymer support can show high selectivity in a hydrogenation reaction of alkyne to alkene by suppressing the hydrogenation reactivity of alkene while maintaining the hydrogenation reactivity of alkyne.

In an exemplary embodiment of the present application, the catalytic component can comprise one or more of platinum (Pt), palladium (Pd), ruthenium (Ru), iron (Fe), nickel (Ni), cobalt (Co), molybdenum (Mo), gold (Au), silver (Ag), copper (Cu), titanium (Ti), gallium (Ga), cerium (Ce), aluminum (Al), zinc (Zn), and lanthanum (La).

In an exemplary embodiment of the present application, a content of the catalytic component can be 0.01 wt % to 10 wt % and 0.05 wt % to 5 wt %, based on a total weight of the catalyst for a hydrogenation reaction. When the content of the catalytic component is less than 0.01 wt % based on the total weight of the catalyst for a hydrogenation reaction, the reactivity of the catalyst can deteriorate. Further, when the content of the catalyst component is more than 10 wt %, a relatively large amount of active metal is contained compared to the polymer support, so that the active metal cannot be easily bonded to the polymer support, and accordingly, the selectivity of alkene is lowered by hydrogenation reaction, so that the actual benefit of the hydrogenation reaction caused by the increase in weight can be decreased.

A method for manufacturing a catalyst for a hydrogenation reaction according to an exemplary embodiment of the present application comprises: preparing a polymer support comprising the repeating unit represented by Formula 1 or 2; and supporting a catalytic component on the polymer support.

In an exemplary embodiment of the present application, the polymer support comprising the repeating unit represented by Formula 1 or 2 can be synthesized by condensation polymerization of a monomer A comprising a triazine structure and a monomer B comprising thiol in a benzene ring. As an example, the monomer A can be a compound containing a cyanuric chloride or a triazine ring and having a functional group capable of nucleophilic aromatic substitution. Further, examples of the monomer B include 1,4-benzenedithiol, 1,3,5-benzenetrithiol, and the like, but are not limited thereto.

In addition, when the polymer support is produced, a basic material can be used in order to remove an acid which can be produced as a result of a condensation polymerization reaction of the monomers A and B, and as the basic material, N,N-diisopropylethylamine (DIPEA), $K_2CO_3$, and the like can be used, but the basic material is not limited thereto. Furthermore, examples of the solvent which can be used in the condensation polymerization reaction of the monomers A and B include an aprotic solvent such as acetonitrile and cyclohexane, but are not limited thereto.

Further, a molar ratio of the monomer A/the monomer B can be 0.5 to 2, and it is possible to include an amount of basic material, which can sufficiently titrate an acid which is produced.

In an exemplary embodiment of the present application, a method for manufacturing the polymer support dissolves both a monomer A and a monomer B in an organic solvent, adds a basic material thereto at 0° C. to 15° C., and reacts the resulting mixture while stirring the mixture at 0° C. to 15° C. for 0.5 hour to 1 hour, 25° C. to 30° C. for 2 hours to 4 hours, and 80° C. to 140° C. for 12 hours to 24 hours. Thereafter, the polymer support can be produced by filtering a produced polymer, washing the filtered polymer with a solvent such as methanol, ethanol, and acetone, and then drying the polymer at 30° C. to 100° C.

In an exemplary embodiment of the present application, in the method for supporting a catalytic component on a polymer support, after an aqueous solution or organic solution (supporting solution) containing a compound as a precursor for the catalytic component is prepared, a catalyst can be synthesized by using an immersion method in which the polymer support is immersed in the supporting solution, dried, and then reduced with hydrogen gas to support the catalytic component, or by stirring the resulting polymer support with metal nanoparticles reduced in advance. As a precursor for the catalytic component, an organic metal compound such as $Pd(acac)_2$, $Pd(NO_3)_2 \cdot 4NH_3$, $Pt(acac)_2$, and $Pt(NO_3)_2 \cdot 4NH_3$ can be used, but the precursor is not limited thereto.

When the catalytic component is supported on the polymer support by the immersion method, an aqueous solution or organic solution is prepared by dissolving a precursor of the catalytic component in water or an organic solvent in a volume corresponding to voids of the polymer support, immersing a polymer support in the solution, completely evaporating the solvent, and drying the resulting product, and then the polymer can be reduced while flowing hydrogen within a temperature at which the polymer is not impaired (<250° C.). Further, after metal nanoparticles reduced in advance are dispersed in an organic solvent, a polymer support is immersed in the solution, the solution is stirred and subjected to ultrasonic treatment. A catalyst can be obtained by filtering the resulting solution until the color of the solution completely fades, and then drying the filtered product.

As an exemplary embodiment of the present application, a method for supporting a catalytic component on a polymer support is schematically illustrated in FIG. 1.

In a method for manufacturing a catalyst for a hydrogenation reaction according to an exemplary embodiment of the present application, details of the polymer support comprising the repeating unit represented by Formula 1 or 2, the catalytic component, and the like are the same as those described above.

The catalyst according to an exemplary embodiment of the present application can be applied to a hydrogenation reaction. For example, the catalyst can be applied to a hydrogenation reaction of alkene from alkyne. The catalyst according to an exemplary embodiment of the present application can be applied not only to acetylene, but also to a hydrocarbon compound having a triple bond. Examples of the hydrocarbon compound include propyne, butyne, pentyne, hexyne, heptyne, octyne, and the like. Furthermore, in a compound comprising a functional group other than the triple bond or a double bond, for example, a compound having a benzene ring such as phenylacetylene, an alkyne compound having a carbonyl group, an alkyne compound having a carbonyl group, an alkyne compound having an alcohol group, an alkyne compound having an amine group, and the like, a hydrogenolysis reaction is suppressed, and only an alkyne group can be applied to a selective hydrogenation reaction to an alkene group.

Hereinafter, the present application will be described in detail with reference to Examples for specifically describing the present application. However, the Examples according to the present application can be modified in various forms, and it is not interpreted that the scope of the present application is limited to the Examples described in detail below. The Examples of the present application are provided for more completely explaining the present application to the person with ordinary skill in the art.

EXAMPLES

<Synthesis Example 1> Synthesis of Polymer Comprising Repeating Unit Represented by Formula 3

2 g of cyanuric chloride (Sigma Aldrich) and 2.4 g of 1,4-dithiol benzene (TCI) were put into 300 mL of 1,4-dioxane (Samchun Chemicals), the resulting solution was stirred, 10 mL of DIPEA (TCI) was added thereto when the solution was completely transparent, and the resulting solution was stirred at 15° C. for 1 hour. Thereafter, the solution was stirred at 25° C. for 2 hours and at 85° C. for 21 hours and filtered, the filtered product was washed with ethanol, and the washed product was sufficiently dried in an oven at 60° C. The produced polymer is represented by "di-S-POL".

<Synthesis Example 2> Synthesis of Polymer Comprising Repeating Unit Represented by Formula 6

A polymer was synthesized in the same manner as in Synthesis Example 1, except that the polymer was synthesized by putting 2.08 g of 1,3,5-trithiol benzene (TCI) thereinto instead of the 1,4-dithiol benzene. The produced polymer is represented by "tri-S-POL".

<Synthesis Example 3> Synthesis of Polymer Comprising Repeating Unit Represented by Formula 4

A polymer was synthesized in the same manner as in Synthesis Example 1, except that 1,3-dithiol benzene was used instead of the 1,4-dithiol benzene.

<Synthesis Example 4> Synthesis of Polymer Comprising Repeating Unit Represented by Formula 5

A polymer was synthesized in the same manner as in Synthesis Example 1, except that 1,2-dithiol benzene was used instead of the 1,4-dithiol benzene.

<Synthesis Example 5> Synthesis of Polymer Comprising Repeating Unit Represented by Formula 7

A polymer was synthesized in the same manner as in Synthesis Example 1, except that 2.6 g of 4-methyl-1,2-dithiol benzene was used instead of the 1,4-dithiol benzene.

<Synthesis Example 6> Synthesis of Polymer Comprising Repeating Unit Represented by Formula 8

A polymer was synthesized in the same manner as in Synthesis Example 1, except that 3.3 g of 4-tert-butyl-1,2-dithiol benzene was used instead of the 1,4-dithiol benzene.

<Experimental Example 1> Structure and Characteristic Analysis of Synthesized Polymer Support In order to confirm the structures of the polymer supports di-S-POL and tri-S-POL produced in Synthesis Examples 1 and 2, a CP/MAS $^{13}$C NMR analysis was performed, and the results thereof are shown in the following FIG. 2. As shown by the data in FIGS. 2A and 2B, respectively, the polymers produced in Synthesis Examples 1 and 2 have structures similar to those of Formulas 3 and 6, respectively.

For the analysis of the physical properties of the polymer support, a differential scanning calorimetry (DSC) analysis was performed, and the results thereof are shown in FIGS. 3A and 3B. As shown in FIGS. 3A and 3B, the polymers produced in Synthesis Examples 1 and 2, respectively, were not cross-linked as in the expected structure, and peaks corresponding to Tm and Tc did not appear.

In order to confirm the thermal stability of the polymer supports, the synthesized polymers were subjected to a thermal gravimetric analysis (TGA) in a hydrogen atmosphere, and the results thereof are shown in FIGS. 4, 9, and 10. More specifically, FIGS. 4A, 4B, 9A, 9B, 10A and 10B are graphical representation of the change in weight of the polymer supports as relates to the temperature in a hydrogen atmosphere, as measured by a thermal gravimetric analyzer. As shown by the results of the thermal gravimetric analysis in FIGS. 4A, 4B, 9A, 9B, 10A and 10B, respectively, the polymers produced in Synthesis Examples 1 to 6 were stable up to about 450° C. in a hydrogen atmosphere.

<Example 1> Synthesis of Catalyst Having Palladium Supported on Polymer Support

1) Synthesis of Palladium Cluster 15 ml of oleylamine and 75 mg of Pd(acac)$_2$ were mixed in an argon atmosphere and stirred at 60° C. for 1 hour. Thereafter, 300 mg of a borane tert-butylamine complex and 3 ml of an oleylamine mixture were put into the aforementioned mixture, and the resulting mixture was heated at 90° C. and stirred for 1 hour. Thereafter, 30 ml of ethanol was put into the mixture, and then a palladium cluster was obtained through centrifugation, and the obtained palladium cluster was dispersed in 20 ml of hexane and stored as a palladium-hexane solution.

2) Supporting Palladium Cluster on Polymer Support 3 g of the polymer support produced in Synthesis Example 1 was each dispersed in 50 mL of hexane, and an amount of reduced palladium nanoparticles equivalent to 0.1 wt % synthesized above was separately dispersed in 50 mL of hexane. The palladium nanoparticle solution was slowly added to the stirring polymer support solution, and the resulting solution was stirred for 30 minutes, and dispersed using a sonicator until the color of the solution became completely transparent. Thereafter, the resulting product was filtered, and then washed with ethanol and dried at room temperature.

<Example 2> Synthesis of Catalyst Having Palladium Supported on Polymer Support

A process was performed in the same manner as in Example 1, except that the polymer support produced in Synthesis Example 2 was used instead of the polymer support produced in Synthesis Example 1.

<Example 3> Synthesis of Catalyst Having Palladium Supported on Polymer Support

A process was performed in the same manner as in Example 1, except that the polymer support produced in Synthesis Example 3 was used instead of the polymer support produced in Synthesis Example 1.

<Example 4> Synthesis of Catalyst Having Palladium Supported on Polymer Support

A process was performed in the same manner as in Example 1, except that the polymer support produced in Synthesis Example 4 was used instead of the polymer support produced in Synthesis Example 1.

<Example 5> Synthesis of Catalyst Having Palladium Supported on Polymer Support

A process was performed in the same manner as in Example 1, except that the polymer support produced in Synthesis Example 5 was used instead of the polymer support produced in Synthesis Example 1.

<Example 6> Synthesis of Catalyst Having Palladium Supported on Polymer Support

A process was performed in the same manner as in Example 1, except that the polymer support produced in Synthesis Example 6 was used instead of the polymer support produced in Synthesis Example 1.

<Comparative Example 1> Synthesis of Catalyst Having Palladium Supported on Silica Support A process was performed in the same manner as in Example 1, except that in Example 1, a commercially available silica (Aldrich, 236772) was used instead of the polymer support produced in Synthesis Example 1. The produced catalyst is represented by "Pd/SiO$_2$".

<Experimental Example 2> Structure and Characteristic Analysis of Catalyst Having Metal Supported on Polymer Support In order to confirm the state of active metals supported on the polymer supports in Examples 1 and 2, a transmission electron microscope (TEM) analysis was performed, and the TEM images are shown in FIGS. 5A and 5B. As shown in the TEM images of FIGS. 5A and 5B, palladium metal particles with a size of about 4 nm were present while being uniformly dispersed in both the Pd/di-S-POL and Pd/tri-S-POL samples, respectively.

In order to confirm the thermal stability of the polymer support catalysts in Examples 1 and 2, the catalyst having palladium supported on the polymer support was subjected to thermal gravimetric analysis (TGA) in a hydrogen atmosphere, and the results thereof are shown in FIGS. 6A and 6B. More specifically, FIGS. 6A and 6B show the change in weight of the catalyst as relates to the temperature in a hydrogen atmosphere, as measured by a thermal gravimetric analyzer. As shown by the results in FIGS. 6A and 6B, the polymers produced in Synthesis Examples 1 and 2, respectively, were stable up to about 250° C. under a hydrogen atmosphere.

<Experimental Example 3> Selective Hydrogenation Reaction of Acetylene Using Supported Catalyst The activities of the supported catalysts produced in the Examples and the Comparative Example were confirmed by the following method.

A hydrogenation reaction of acetylene was performed under conditions of 1 atm, 60° C., and a weight hourly space velocity (WHSV) of 0.021 to 1.25 $g_{C2H2} g_{cat}^{-1} h^{-1}$ by feeding 0.6 kPa of acetylene, 49.3 kPa of ethylene, and 0.9 kPa of hydrogen- and nitrogen-based gases.

In order to analyze product components in the hydrogenation reaction, the product components were analyzed using gas chromatography. The conversion of a reactant (acetylene) and the selectivity of products (ethylene, ethane, and the like) were calculated by the following Equations 1 and 2:

Conversion (%) = [Equation 1]
(the number of moles of acetylene reacted)/
(the number of moles of acetylene fed) × 100;

Selectivity (%) = [Equation 2]
(the number of moles of product produced)/
(the number of moles of acetylene reacted) × 100.

The acetylene hydrogenation reaction results using the catalysts produced in Examples 1 and 2 are shown in the following Table 1 and FIGS. 7 and 8. More specifically, FIG. 7 is a graphical representation of the selectivity of ethylene as relates to the value of the acetylene conversion, and FIG. 8 is a graphical representation of the conversion of acetylene as relates to the value of 1/WHSV.

Analysis devices and analysis conditions applied in the present application are as follows.

1) Cross polarization magic-angle spinning $^{13}C$ nuclear magnetic resonance (CP/MAS $^{13}C$ NMR):
Used equipment: Avance III HD (400 MHz) with wide bore 9.4 T magnet (Bruker).
Analysis method: Larmor frequency of 100.66 MHz, repetition delay time of 3 seconds. Chemical shifts were reported in ppm relative to tetramethyl silane (0 ppm).

2) Differential scanning calorimetry (DSC):
Used equipment: DSC131 evo (Setaram).
Analysis method: After a sample was placed on an alumina pan, the conversion was measured by regulating the temperature at a rate of 5 K/min from 313 K to 593 K.

3) Transmission electron microscope (TEM):
Used equipment: JEM-2100F (JEOL) at 200 kV.

4) Thermal gravimetric analysis (TGA):
Used equipment: TGA N-1000 (Scinco).
Analysis method: the conversion was measured by increasing the temperature at 5 K/min from 323 K to 1,025 K. 5) Gas chromatography (GC):
Used equipment: YL6500 (Youngin).
Analysis method: on-line GC, equipped with flame ionized detector (FID), GS-GasPro (Agilent) column was used.

TABLE 1

| Type of catalyst | WHSV ($g_{C2H2} g_{cat}^{-1} h^{-1}$) | Acetylene Conversion (%) | Ethane Selectivity (%) | Ethylene Selectivity (%) | Others (C$_4$) Selectivity (%) |
|---|---|---|---|---|---|
| Example 1 | 0.021 | 100 | 23.0 | 60.2 | 16.8 |
| Example 1 | 0.10 | 100 | 29.1 | 53.9 | 17.0 |
| Example 2 | 0.021 | 100 | 15.3 | 68.4 | 16.3 |
| Example 2 | 0.10 | 100 | 24.7 | 59.5 | 15.8 |
| Example 3 | 0.021 | 100 | 22.8 | 60.5 | 16.7 |
| Example 4 | 0.021 | 100 | 22.6 | 61.2 | 16.2 |
| Example 5 | 0.021 | 100 | 23.7 | 59.8 | 16.5 |
| Example 6 | 0.021 | 100 | 22.6 | 61.0 | 16.4 |
| Comparative Example 1 | 0.021 | 100 | 32.8 | 50.9 | 16.3 |

As shown by the Results in Table 1 and FIGS. 7 and 8, that the catalyst (Pd/di-S-POL) of Example 1, the catalyst (Pd-tri-S-POL) of Example 2, and the catalysts of Examples 3 to 6, which are catalysts for a hydrogenation reaction according to exemplary embodiments of the present application, exhibit high ethylene selectivity even at high conversion and have better ethylene selectivity than the catalyst (Pd/SiO$_2$) of Comparative Example 1 at the same hourly space velocity.

From the experimental results using the polymer support comprising the repeating unit represented by any one of Formulae 3 to 8, similar effects can be obtained even when a functional group such as another alkyl group and aryl group having a similar action principle is additionally bonded to a repeating unit represented by Formula 1 or 2.

Therefore, according to an exemplary embodiment of the present application, a polymer support comprising the repeating unit represented by Formula 1 or 2 can be applied as a support of a catalyst for a hydrogenation reaction.

Further, according to an exemplary embodiment of the present application, the catalyst comprising the polymer support is characterized by having excellent stability in the reaction temperature range of the hydrogenation reaction and being able to improve the selectivity for the product of the hydrogenation reaction.

The invention claimed is:
1. A catalyst for a hydrogenation reaction, the catalyst comprising:

a polymer support; and a catalytic component supported on the polymer support,
wherein the polymer support consists of a repeating unit represented by [Formula 4], wherein the wave bond "⁓" in the [Formula 4] means a point where the repeating units are linked:

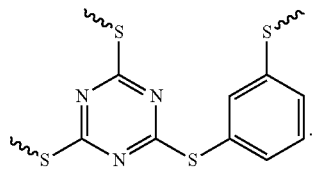

[Formula 4]

2. The catalyst of claim 1, wherein the catalytic component comprises one or more of platinum, palladium, ruthenium, iron, nickel, cobalt, molybdenum, gold, silver, copper, titanium, gallium, cerium, aluminum, zinc, and lanthanum.

3. The catalyst of claim 1, wherein an amount of the catalytic component is 0.01 wt % to 10 wt % based on a total weight of the catalyst for a hydrogenation reaction.

4. The catalyst of claim 1, wherein the catalyst for a hydrogenation reaction is a catalyst for a hydrogenation reaction of alkyne to alkene.

5. A method for manufacturing a catalyst for a hydrogenation reaction, the method comprising:

preparing a polymer support consisting of a repeating unit represented by [Formula 4], wherein the wave bond "⁓" in the [Formula 4] means a point where the repeating units are linked; and supporting a catalytic component on the polymer support:

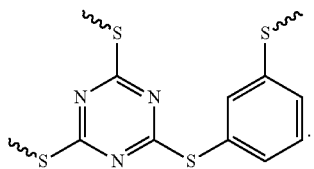

[Formula 4]

6. The method of claim 5, wherein the catalytic component comprises one or more of platinum, palladium, ruthenium, iron, nickel, cobalt, molybdenum, gold, silver, copper, titanium, gallium, cerium, aluminum, zinc, and lanthanum.

7. The method of claim 5, wherein an amount of the catalytic component is 0.01 wt % to 10 wt % based on a total weight of the catalyst for a hydrogenation reaction.

* * * * *

UNITED STATES PATENT AND TRADEMARK OFFICE
CERTIFICATE OF CORRECTION

| | | |
|---|---|---|
| PATENT NO. | : 11,872,546 B2 | Page 1 of 1 |
| APPLICATION NO. | : 17/432455 | |
| DATED | : January 16, 2024 | |
| INVENTOR(S) | : Suh et al. | |

It is certified that error appears in the above-identified patent and that said Letters Patent is hereby corrected as shown below:

On the Title Page

Item (73) The Assignee field should recite:
Assignees: LG Chem, Ltd., Seoul (KR); Korea Advanced Institute of Science and Technology, Daejeon (KR)

Signed and Sealed this
Seventh Day of January, 2025

Derrick Brent
*Acting Director of the United States Patent and Trademark Office*